United States Patent [19]

Meilland

[11] Patent Number: Plant 6,385

[45] Date of Patent: Nov. 8, 1988

[54] ROSE PLANT—MEIRANOVI VARIETY

[75] Inventor: Marie-Louise Meilland, Antibes, France

[73] Assignee: The Conard-Pyle Company, West Grove, Pa.

[21] Appl. No.: 895,491

[22] Filed: Aug. 11, 1986

[51] Int. Cl.[4] ..... A01H 5/00

[52] U.S. Cl. ..... Plt./1

[58] Field of Search ..... Plt./1, 26–27

*Primary Examiner*—Robert E. Bagwill

*Attorney, Agent, or Firm*—Burns, Doane, Swecker & Mathis

[57] ABSTRACT

A new and distinct variety of shrub rose plant is provided which forms attractive semi-double pink blossoms. The new variety exhibits an arching and flowing growth habit and is well adapted for growing in the landscape. Excellent disease resistance and hardiness also are exhibited.

2 Drawing Sheets

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) of the new variety was formed by crossing *Rosa sempervirens* with the Marthe Carron variety. The male parent (i.e., the pollen parent) of the new variety was formed by a series of crosses. The Lili Marlene variety was crossed with the Evelyne Fison variety (U.S. Plant Pat. No. 2,424). The product of this cross was then crossed with the product of a cross between the Orange Sweetheart variety (U.S. Plant Pat. No. 1,155) and the Frühlingsmorgen variety to form the male parent. The parentage of the new variety can be summarized as follows:

[*Rosa sempervirens*×MARTHE CARRON]×[(LILI MARLENE×EVELYNE FISON)×(ORANGE SWEETHEART×FRüHLINGSMORGEN)].

The seeds resulting from the above pollination were sown and 191 plantlets were obtained which were physically and biologically different from each other. Selective study resulted in the identification of a single plant of the new variety.

It was found that the new variety of shrub rose plant of the present invention possesses the following combination of characteristics:

(a) forms attractive semi-double pink blossoms,
(b) exhibits a flowing growth habit which forms a plant having a greater width than height,
(c) exhibits excellent disease resistance,
(d) exhibits excellent hardiness,
(e) exhibits a propensity to readily undergo asexual propagation from cuttings, and
(f) is particularly well suited for growing in the landscape.

The new variety meets the needs of the horticultural industry for all uses. It can be grown to advantage as an attractive ornamentation in parks, gardens, public areas, and residential landscapes.

The new variety has been found to undergo asexual propagation by a number of routes, including the use of cuttings, budding and grafting. The characteristics of the new variety have been found to be extremely uniform and homogeneous and are strictly transmissible by such asexual propagation from one generation to another.

The new variety has been named the Meiranovi variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein (except where otherwise indicated) were two years of age and were grown outdoors on *Rosa froebelii* understock at Cannet des Maures, Var, France. The color of the fully opened blossoms is more accurately illustrated in FIG. 13 than in the other photographs.

FIG. 6 illustrates a specimen of floral receptacle showing the arrangement of the stamens and pistils (sepals removed);

FIG. 8 illustrates a specimen of a main branch;

DETAILED DESCRIPTION

Figures 1, 2, 3, 4, 5, 7, 9, 10, 11, 12:
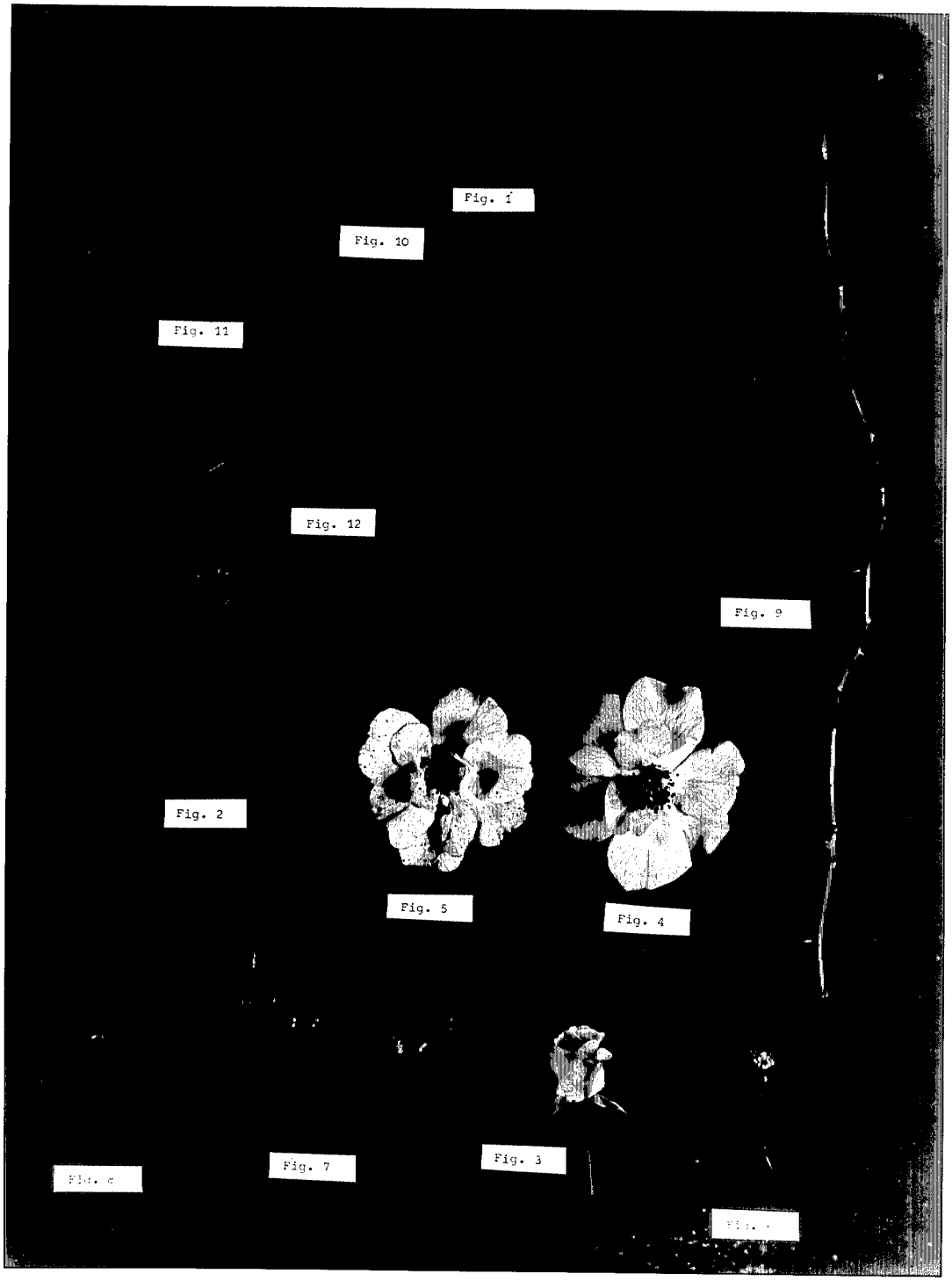
FIG. 1 illustrates a specimen of a young shoot.
FIG. 2 illustrates a specimen of five flowering buds showing four buds before the opening of the sepals and one bud after the opening of the sepals.
FIG. 3 illustrates a specimen of a flowering bud at the opening of the petals.
FIG. 4 illustrates a specimen of a fully open flower—plan view—obverse.
FIG. 5 illustrates a specimen of a fully open flower immediately prior to petal drop—plan view—obverse.
FIG. 7 illustrates four specimens of fruits on a floral branch.
FIG. 9 illustrates a specimen of a flowering stem.
FIG. 10 illustrates a specimen of a leaf with three leaflets—under surface.
FIG. 11 illustrates a specimen of a leaf with five leaflets—upper surface.
FIG. 12 illustrates a specimen of a leaf with seven leaflets—upper surface.
Figure 13:
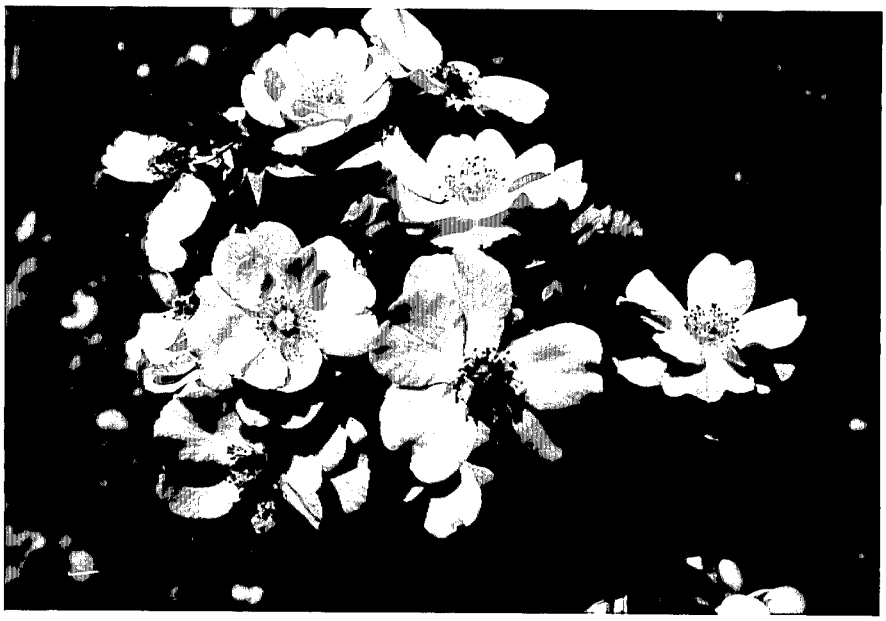
FIG. 13 illustrates specimens of buds and fully opened blossoms in which the coloration is more accurately illustrated.
Figure 14:
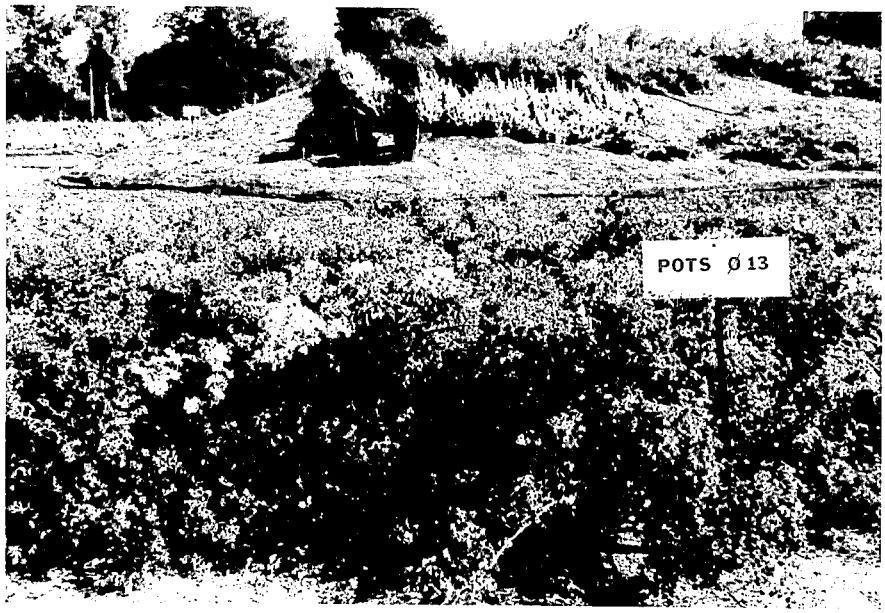
FIG. 14 illustrates during mid-June the general growth habit of eight three year old plants growing in the South of France, wherein the sign post is approximately 80 cm. in height.

The chart used in the identification of the colors is that of the Royal Horticultural Society (R.H.S. Colour Chart). The terminology preceding the numbered references has been added to designate in common terms the corresponding colors. The description is based on two-year old specimens of the new variety while budded on *Rosa froebelii* understock and grown outdoors at Cannet des Maures, Var, France.

Class: Shrub.

Plant:

*Height.*—Approximately 60 cm. on average.

*Habit.*—Arching and flowing, has a greater width than height.

Branches:

*Color.*—Young stems: Yellow-Green Group 146B. Adult wood: Yellow-Green Group 146A.

Leaves:

*Petioles.*—Upper surface: grooved, slightly reddish on young foliage, medium green on adult foliage. Under surface: light green with several small thorns.

*Leaflets.*—Number: 3, 5, and 7 (most often). Shape: elliptic. Serration: simple and regular. Color (young foliage): upper surface: dark bronze green, Yellow-Green Group 135A; under surface: light yellow green, Yellow-Green Group 146C. Color (adult foliage): upper surface: Yellow-Green Group 131A; under surface: Yellow-Green Group 147B.

Inflorescence:

*Number of flowers.*—Approximately 1 to 23 per stem.

*Peduncle.*—Its length is approximately 2 to 3 cm. on average.

*Buds.*—Shape: conical before the opening of the sepals. Length: approximately 1.5 cm. on average. Color: upper surface: Red Group 50B; under surface: Red Group 52A.

*Flower.*—Form: semi-double. Diameter: approximately 5.5 cm. on average. Color (when opening begins): upper surface: Red Group 47D; under surface: Red Group 54A. Color (when partially open): upper surface: Red Group 50C; under surface: Red Group 54B. Color (at end of opening): upper surface: Red Group 50C; under surface: Red Group 55C. Fragrance: none. Petal number: approximately 15 on average, commonly several of these are not complete. Stamen number: approximately 77 on average. Pistils: approximately 28 on average.

Development:

*Hardiness.*—Excellent.

*Disease resistance.*—Excellent.

I claim:

1. A new and distinct variety of shrub rose plant characterized by the following combination of characteristics:

(a) forms attractive semi-double pink blossoms, (b) exhibits a flowing growth habit which forms a plant having a greater width than height, (c) exhibits excellent disease resistance, (d) exhibits excellent hardiness, (e) exhibits a propensity to readily undergo asexual propagation from cuttings, and (f) is particularly well-suited for growing in the landscape;

substantially as herein shown and described together with the parts thereof.

* * * * *